United States Patent
Darwish et al.

(10) Patent No.: US 11,821,972 B2
(45) Date of Patent: Nov. 21, 2023

(54) METHOD AND SYSTEM FOR SYNCHRONIZING A ROTATIONAL ECCENTRIC MASS WITH A MAGNETIC RESONANCE ELASTOGRAPHY SCAN

(71) Applicants: Siemens Healthcare GmbH, Erlangen (DE); Centre National de la Recherche Scientifique (CNRS), Paris (FR); Institut National de La Sante et de la Recherche Medicale (INSERM), Paris (FR); King's College London, London (GB); Department of Health and Human Services, Bethesda, MD (US); UNIV PARIS XIII PARIS-NORD VILLETANEUSE, Villetaneuse (FR); Universite de Paris, Paris (FR)

(72) Inventors: Omar Darwish, London (GB); Radhouene Neji, London (GB); Ahmed M. Gharib, Bethesda, MD (US); Ralph Sinkus, Parmain (FR)

(73) Assignee: Siemens Healthcare GmbH, Erlangen (DE)

( * ) Notice: Subject to any disclaimer, the term of this patent is extended or adjusted under 35 U.S.C. 154(b) by 38 days.

(21) Appl. No.: 17/702,212

(22) Filed: Mar. 23, 2022

(65) Prior Publication Data
US 2023/0305090 A1   Sep. 28, 2023

(51) Int. Cl.
*G01R 33/30* (2006.01)
*G01R 33/563* (2006.01)
(Continued)

(52) U.S. Cl.
CPC ....... *G01R 33/56358* (2013.01); *G01R 33/30* (2013.01); *H02P 8/08* (2013.01); *H02P 8/22* (2013.01)

(58) Field of Classification Search
CPC ..... G01R 33/56358; G01R 33/30; H02P 8/08; H02P 8/22
See application file for complete search history.

(56) References Cited

U.S. PATENT DOCUMENTS

2018/0271376 A1* 9/2018 Feng ................ G01R 33/56358
2018/0292501 A1* 10/2018 Neumann ............... B06B 1/186

OTHER PUBLICATIONS

Parker, K.J.; Doyley, M.M.; Rubens D.J.: "Imaging the elastic properties of tissue: the 20 year perspective", in: Phys Med Biol. Jan. 7, 2011;56(1):R1-R29, Nov. 30, 2010.doi: 10.1088/0031-9155/56/1/R01. Erratum in: Phys Med Biol. Aug. 21, 2012;57(16):5359-60. PMID: 21119234.

(Continued)

*Primary Examiner* — Jermele M Hollington
*Assistant Examiner* — Taqi R Nasir
(74) *Attorney, Agent, or Firm* — Banner & Witcoff Ltd.

(57) ABSTRACT

The present disclosure is directed to techniques for synchronizing a rotational eccentric mass of a gravitational transducer used for a magnetic resonance elastography acquisition with a corresponding magnetic resonance elastography scan carried out by a magnetic resonance imaging system, wherein the rotation of the eccentric mass is driven by a shaft. The method includes starting the rotation of the eccentric mass at a set vibration frequency and the magnetic resonance elastography scan at a set acquisition frequency; determining the rotational position of the shaft; defining the rotational position as first reference position; calculating further reference positions. At the start time of each subsequent acquisition period, determining the current rotational position of the shaft; comparing the determined current rotational position with the theoretically expected reference position and decreasing or increasing the rotational speed of the rotational eccentric mass based on the comparison.

14 Claims, 6 Drawing Sheets

(51) Int. Cl.
   *H02P 8/22*   (2006.01)
   *H02P 8/08*   (2006.01)

(56) References Cited

OTHER PUBLICATIONS

Dittmann, F.; Tzschätzsch, H. et al: "Tomoelastography of the Abdomen: Tissue Mechanical Properties of the Liver, Spleen, Kidney, and Pancreas From Single MR Elastography Scans at Different Hydration States", in: Magn. Reson. Med., 78: 976-983, 2017. https://doi.org/10.1002/mrm.26484.
Yin, M.; Talwalkar, J.A. et al.: "Assessment of hepatic fibrosis with magnetic resonance elastography", in: Clin. Gastroenterol. Hepatol. 5 1207-1213, 2007. doi:10.1016/j.cgh.2007.06.012.
Runge J. et al.:"A novel magnetic resonance elastography transducer concept based on a rotational eccentric mass: preliminary experiences with the gravitational transducer" Physics in Medicine & Biology, 64(4), 045007.
Magnetic resonance elastography by direct visualization of propagating acoustic strain waves; Muthupillai, R. et al.
Neumann Wiebke et al: "A Novel 3D Printed Mechanical Actuator Using Centrifugal Force for Magnetic Resonance Elastography: Initial Results In An Anthropomorphic Prostate Phantom", —Place of search mechanical actuator using One, vol. 13, No. 10, Oct. 8, 2018 (Oct. 8, 2018), p. e0205442, XP093063711, DOI:10.1371/journal.pone.0205442.

* cited by examiner

METHOD AND SYSTEM FOR SYNCHRONIZING A ROTATIONAL ECCENTRIC MASS WITH A MAGNETIC RESONANCE ELASTOGRAPHY SCAN

TECHNICAL FIELD

The invention relates to a method for synchronizing a rotational eccentric mass of a gravitational transducer used for a magnetic resonance elastography acquisition with a corresponding magnetic resonance elastography scan, a method for executing a magnetic resonance elastography scan of a subject, a stepper motor configured to drive a rotational eccentric mass of a gravitational transducer for a magnetic resonance elastography, a magnetic resonance imaging system and a corresponding non-transitory computer-readable medium having stored thereon a corresponding computer program product.

BACKGROUND

Magnetic Resonance Elastography (MRE) typically comprises applying mechanical stress, for example via vibrations, to a tissue of a subject and measuring the response of the tissue via magnetic resonance imaging (MRI). This allows detecting mechanical properties of the tissue that are otherwise not accessible via MRI. Thus, MRE enables non-invasive estimation of biomechanical parameters in tissues. Biomechanical parameters, such as elasticity and viscosity, receive a growing clinical interest, in particular in the domain of liver fibrosis quantification. Liver fibrosis is triggered by prolonged inflammation. Therefore, the simultaneous staging of both inflammation and fibrosis is important for an efficient patient management.

In Yin M., Talwalkar J. A., Glaser K. J., Manduca A., Grimm R. C., Rossman P. J., Fidler J. L. and Ehman R. L.: "Assessment of hepatic fibrosis with magnetic resonance elastography", Clin. Gastroenterol. Hepatol. 5, pp. 1207-13 (2007), and in Dittmann, F., Tzschätzsch, H., Hirsch, S., Barnhill, E., Braun, J., Sack, I. and Guo, J., "Tomoelastography of the abdomen: Tissue mechanical properties of the liver, spleen, kidney, and pancreas from single MR elastography scans at different hydration states", Magn. Reson. Med. 78: pp. 976-983 (2017), it is proposed to use pneumatics and compressed air, respectively, for mechanical excitation for MRE. However, at least for some applications, it would be beneficial to increase the linearity and reduce parasitic harmonics.

In Runge J. H., Hoelzl S. H., Sudakov J. et al., "A novel magnetic resonance elastography transducer concept based on a rotational eccentric mass: preliminary experiences with the gravitational transducer", Phys. Med. Biol. 64:045007 (2019), the use of a gravitational transducer setup is used for excitation. This publication is herewith incorporated herein by reference. The gravitational transducer is based on a rotational eccentric mass, wherein the rotation of the eccentric mass is used to excite vibrations. Via this setup it is possible to achieve a greater linearity and reduced parasitic harmonics. However, it has been found by the applicant that at least for some applications it would be beneficial to increase the stability and synchronization of the gravitational transducer and the mechanically induced excitation of the tissue with the MRI system. In particular, the stability of the angular position of the eccentric mass throughout the MRE acquisition is very important to achieve reliable and stable measurement results.

It is therefore an object of the invention to provide a method and system for carrying out magnetic resonance elastography with a linearity comparable to the method using a gravitational transducer while at the same time improving the stability of the mechanical excitations and their synchronization with the magnetic resonance imaging.

SUMMARY

This object is met or exceeded by a method according to claim 1, a method according to claim 10, a stepper motor according to claim 11, a magnetic resonance imaging system according to claim 12, and a non-transitory computer-readable medium according to claim 14.

According to a first aspect of the invention, a method for synchronizing a rotational eccentric mass of a gravitational transducer used for a magnetic resonance elastography acquisition with a corresponding magnetic resonance elastography scan carried out by a magnetic resonance imaging system is provided. Therein, the rotation of the eccentric mass is driven by a shaft. The method comprises the steps: (a) starting the rotation of the eccentric mass at a set vibration frequency and the magnetic resonance elastography scan at a set acquisition frequency, wherein the vibration frequency is set such that one or an integer number of rotational periods of the eccentric mass equals an acquisition period, wherein the integer number is the burst count; (b) at a start time of an acquisition period of the magnetic resonance scan, determining the rotational position of the shaft; (c) defining the determined rotational position as first reference position, which the shaft is theoretically expected to occupy at the start time of at least some of the subsequent acquisition periods; (d) depending on the burst count, calculating further reference positions that the shaft is theoretically expected to occupy at the start time of each subsequent acquisition period, wherein the further reference positions may be the same as the first reference position, or may alternate between several positions; (e) at the start time of each subsequent acquisition period of the magnetic resonance scan, determining the current rotational position of the shaft; (f) after each determination of the current rotational position, comparing the determined current rotational position with the theoretically expected reference position and decreasing or increasing the rotational speed of the rotational eccentric mass based on the comparison.

Advantageously defining at least one reference point and adjusting the rotational speed of the eccentric mass allows to compensate for the gravitational transducer rotating less reliably and/or with a slightly different speed than the accuracy of the acquisition frequency. In principle, stabilizing the gravitational transducer may thus be achieved by comparing the current position of the shaft and the one or multiple reference positions defined at the beginning of the MRE examination, and then speedup or slowdown the input shaft accordingly. In particular, a system or method of capturing the reference positions depending on the burst-count of the MRE acquisition is provided.

The gravitational transducer may be configured to be attachable to a subject, in particular to a side of the subject. The gravitational transducer may comprise a housing and the rotational eccentric mass may be arranged within the housing. The rotational eccentric mass may be attached to a rotatable axis that is connected to at least one inner wall of the housing. In particular, the end points of the rotatable axis may be attached to opposite walls of the housing. The eccentric mass may be configured such that it rotates around the rotatable axis when the rotatable axis is rotated. The eccentric mass may be connected to the shaft, in particular via the rotatable axis. The shaft may be connected to the rotatable axis, in particular via a gear mechanism. The eccentric mass is preferably configured such that when it is rotated it is kept on its plane of rotation by a centripetal force that is translated to the housing of the gravitational transducer. This may advantageously result in a time-varying force in all directions vertical to the rotatable axis which may cause the gravitational transducer to rotate at the frequency of the rotation of the eccentric mass. The concept of the gravitational transducer may be explained by the following equations. Therein, the centripetal force holding the eccentric mass that rotates at frequency fvib is:

$$F(t) = -mr\omega^2 e^{i(\emptyset + t\omega)}$$

where m is the mass of the eccentric mass, r is the distance from the center of gravity of the eccentric mass to the axis of rotation, co is the angular frequency ($2\pi$ f vib) and $\emptyset$ is an arbitrary phase. According to Newton's third law and since the rotatable axis is held by the housing of the gravitational transducer, an equal and opposing force will act on the whole gravitational transducer, with the mass of the gravitational transducer being M+m:

$$\frac{dx^2}{dt^2} = -\frac{F(t)}{M+m}$$

Thus, during operation, the displacement of the gravitational transducer and its amplitude may be given by:

$$x(t) = -\frac{m}{M+m} r e^{i(\emptyset + t\omega)}$$

$$|x(t)| = \frac{m}{M+m} r$$

The gravitational transducer may be controlled using a motor controller center, such as MCC-1-32-48-USB-W-B MINI as described in Yin M., Talwalkar J. A., Glaser K. J., Manduca A., Grimm R C., Rossman P. J., Fidler J. L. and Ehman R L "Assessment of hepatic fibrosis with magnetic resonance elastography" Clin. Gastroenterol. Hepatol. 5: 1207-13 (2007). The determining of the rotational position of the shaft may be controlled by the controller center. For example, the motor controller center may supervise the rotation of the shaft and/or of a motor driving the shaft. In particular, the rotational position of the rotational shaft may be determined by the motor controller center or a control unit of the motor controller center. The controller center may be controlling one, some or all of the further steps of the method as well. In particular the controller center may carry out the steps of comparing the determined current rotational position with the theoretically expected reference position and the decreasing or increasing of the rotational speed of the rotational eccentric mass.

The vibration frequency of the eccentric mass may be set via setting the speed of a motor driving the shaft. The vibration frequency is preferably the frequency at which the eccentric mass is rotated. The acquisition frequency is preferably the frequency at which an acquisition of data by the magnetic resonance elastography scan is carried out, such as a frequency that is characteristic for the imaging sequence used in the MRE scan, for example it may be related to the repetition time TR and/or the echo time TE. In particular, the acquisition frequency may be the frequency of acquisition of k-space lines. In other words, the acquisition frequency may be related to and/or be the acquisition rate of the k-space lines, in particular such that the acquisition frequency equals the number of k-space lines acquired per second. Advantageously, by setting the vibration frequency such that one or an integer number n of rotational periods of the eccentric mass equals an acquisition period, an excitation of tissue via the gravitational transducer may be synchronized with the magnetic resonance elastography scan more easily. Hence, there may be an integer number n (n being 1, 2, 3, . . . , up to 10) of excitations or wave periods caused by the gravitational transducer during each characteristic period of acquisition, e.g., during each acquisition of one k-space line. In other words, the burst count may be the number of mechanical wave periods and/or the number of rotations of the eccentric mass required for one acquisition period, in particular required to acquire one k-space line. The number of reference positions may depend on the burst count and/or on a gear ratio between the shaft and the eccentric mass. The start time of an acquisition period of the magnetic resonance scan in step b) may be the start time of the first acquisition period. Alternatively, the start time may be the start time of another acquisition period, in particular at a time after the eccentric mass has been accelerated to full speed or approximately to full speed Approximately to full speed may mean, e.g., within at least 90% of full speed, preferably within at least 95% of full speed.

The determined rotational position of the shaft is defined as first reference position. Since, depending on the scan that is to be carried out, it may be beneficial to apply different speeds of the eccentric mass relative to the acquisition frequency and since the gear ratio of the shaft and the eccentric mass may be unequal 1, the position of the shaft may vary at the start point of each acquisition period. Thus, it may be beneficial to choose different reference positions which depend on the burst count. The reference position and/or the further reference positions are in particular the positions that the shaft would occupy if the vibration frequency or an integer multiple of the vibration frequency was exactly equal to the acquisition frequency. Since the acquisition frequency is typically more precise than the vibrational frequency, the inventive method may thus correct timing deviations between both frequencies by decreasing or increasing the rotational speed of the rotational eccentric mass at each start time of each acquisition period based on the comparison between the reference position and the current position. Thus, after setting the reference position, the speed of the gravitational transducer may be adapted throughout the whole magnetic resonance elastography examination depending on the reference position. This may advantageously ensure the phase stability of the gravitational transducer According to an embodiment, after starting the rotation of the rotational eccentric mass and the magnetic resonance scan, a predetermined number of acquisition periods is discarded as dummy shots before the rotational position of the shaft is determined at the start time of a further acquisition period. The number of dummy shots may be predetermined based on the time the rotational eccentric mass needs to accelerate to full set rotational speed or approximately full set rotational speed. "Approximately full set rotational speed" may mean at least 90%, preferably at least 95%, of full speed. The number of dummy shots may be chosen such that the time of the dummy shots combined acquisition periods is equal and/or at least as long as the time the rotational eccentric mass needs to accelerate to full set rotational speed or approximately full set rotational speed. For example, 2 to 6, in particular 4, k-space line acquisition shots may be discarded as dummy shots. It has turned out that 2 to 6 dummy shots are sufficient to achieve stable results for many applications, wherein 4 dummy shots are a good value for many most relevant acquisitions. Advantageously, the application of dummy shots may allow to accelerate the gravitational transducer to the required frequency of the magnetic resonance elastography (MRE) examination. The required frequency may for example be in the range of 40 to 100 Hz, in particular about 60 Hz. During the dummy shots the MRE system may send signals to a control unit of the gravitational transducer or of the motor driving the gravitational transducer in order to communicate the start of the MRE examination, and in particular trigger the start of the rotation of the eccentric mass. The first reference position may be determined after, preferably directly after, the last dummy shot at the start of the next acquisition shot.

According to an embodiment, in step (f), the rotational speed of the shaft is increased if the difference between the respective reference position and the actual current position is greater than zero and greater than $\pi$ or if the difference between the respective reference position and the actual current position is less than zero and greater than $-\pi$. On the other hand, in step (f), the rotational speed of the shaft is decreased if the difference between the respective reference position and the actual current position is greater than zero and less than $\pi$ or if the difference between the respective reference position and the actual current position is less than zero and less than $-\pi$. Advantageously this may allow to reliably stabilize the gravitational transducer. Advantageously these adjustments may provide a means to stabilize the gravitational transducer, while avoiding phase wrapping effects that might come into place otherwise. Setting R* to be $R^*$=reference position−current position the process of stabilizing may alternatively be formulated with the following terms:

$$\text{if } R^* > 0 \begin{cases} \text{speedup if } R^* > \pi \\ \text{slowdown if } R^* < \pi \end{cases}$$

$$\text{if } R^* < 0 \begin{cases} \text{speedup if } R^* > -\pi \\ \text{slowdown if } R^* < -\pi \end{cases}$$

This embodiment takes into account the wrapping of the position if it goes above $2\pi$ radians or below 0 radians, which may be taken care of by the constraint conditions as described here.

According to an embodiment, the shaft is driven by a stepper motor, and/or the rotation of the shaft is transferred to the gravitational transducer via a flexible rotating axis. The stepper motor may comprise the motor control center as described above and/or comprise a control unit which may for example be part of the motor control center. The motor control center and/or the control unit may comprise instructions to be initiate carrying out of at least some of the method steps. The stepper motor may be arranged outside an examination room. Accordingly, the determination of the current rotational position of the shaft may also be carried out outside the examination room, in particular in and/or by the stepper motor. The stepper motor may be configured to carry out a number of micro steps per rotation of the shaft, wherein the number of micro steps per shaft rotation may be in the range of 100 to 3000, preferably in the range of 200 to 200, more preferably in the range of 500 to 1000, and most preferably in the range of 700 to 900. The flexible rotating axis may be the same as described in Runge J. H., Hoelzl S. H., Sudakov J. et al., "A novel magnetic resonance elastography transducer concept based on a rotational eccentric mass: preliminary experiences with the gravitational transducer", Phys. Med. Biol. 64:045007 (2019).

According to an embodiment, in step (f) the rotational speed of the shaft is increased or decreased by a fixed amount in each acquisition period. The fixed may be measured in micro steps of the stepper motor. For example, the fixed amount may be in the range of 1 to 100, preferably 3 to 50, more preferably 5 to 20, micro steps. The fixed amount may preferably correspond to a fraction of the frequency of the shaft. A fixed amount may be easier to implement than a varying amount. Accordingly, the current position may advantageously be controlled to fluctuate around the set reference positions with only small fluctuations depending on the fixed amount.

According to an embodiment, the rotation of the shaft is translated to rotational eccentric mass of the gravitational transducer with a gear ratio of 1 or higher, preferably of 2 or higher, e.g. up to 8, such that the rotational eccentric mass rotates faster than the shaft. Thus, for example, a faster rotation than the frequency of the stepper motor may be achieved. For example, the shaft, in particular the flexible rotating axis driven by the stepper motor, may rotate at a certain frequency such as f vib/3. The rotation may be translated through the flexible rotating axis to the axis of the eccentric mass with a gear ratio of, e.g., 1 to 3 to rotate the eccentric mass at a frequency f vib. Thus, vibrations of the gravitational transducer with a frequency of f vib may be achieved.

According to an embodiment, in step (d), the further reference positions that the shaft is theoretically expected to occupy at the start time of each subsequent acquisition period is determined on the basis of the burst-count and the gear ratio. Since the burst count describes the number of rotations of the eccentric mass during one acquisition period, the nominal rotational position of the shaft may be different from zero degree at some instances depending on the gear ratio between the shaft's rotation and the rotation of the eccentric mass. The method may implement a logical system of handling the different possibilities of burst-count modes. For example, the gear ratio may be 3. It has turned out that a gear ratio of 3 may to be suitable to deliver good results in the case of a liver gravitational transducer. For a gear ratio of 3 the number of reference positions may be 1 or 3. In this example, i.e., with a gear ratio of 3, e.g., for a burst count of 3, the burst count modulo 3 equals 0. Accordingly, there is only one reference position. The shaft (rotating at f vib/3) will go back to be in the same rotational position after 3, 6, 9, 12 mechanical periods (which are integer multiples of the burst count) of the eccentric mass (rotating at f vib). Further, in the case of a burst count modulo 3 equals 1, such as with a burst count of 4, there are three reference positions for a gear ratio of 3. In this case the reference positions may alternate between the first reference position, a second reference position, which is the first reference position+$2\pi/3$, and a third reference position, which is the first reference position+$4\pi/3$. Finally, in the case of a burst count modulo 3 equals 2, such as with a burst count of 5, there are also three reference positions for a gear ratio of 3. In this case the reference positions may alternate between the first reference position, a second reference position, which is the first reference position+$4\pi/3$, and a third reference position, whit is the first reference position+$2\pi/3$. The control unit and/or the motor controller center may be configured to automatically adapt the determining of reference positions based on the burst count and the gear ratio. According to an embodiment, if the gear ratio is three and a burst count modulo 3 is 0, the further reference positions are the same as the first reference positions, and if the burst count modulo 3 is 1 or 2, the further reference positions alternate between three different rotational positions. In particular, if the gear ratio is three and the burst count is 3, the further reference positions are the same as the first reference positions, and if the burst count is 4 or 5, the further reference positions alternate between three different rotational positions.

According to an embodiment, step (e) is triggered by a signal received from the magnetic resonance imaging system at the start time of each acquisition cycle, in particular a transistor-transistor-logic (TTL). Such a signal may be generated by the same component of the MRI system that clocks/controls the timing of the MRE imaging sequence. Thereby, the signal is extremely accurate, since the gradients and RF pulses required for MR imaging are generally timed extremely accurately. The signal may for example be sent whenever the MRI system is instructed to receive an MR signal, e.g. when the Analogue-to-Digital converters (ADC's) are set to "ON" in order to acquire a k-space line.

At the beginning of the acquisition the MRE sequence of the MRI system may send TTLs without any imaging gradients and discard these shots as dummy shots. Said TTLs may be received by the gravitational transducer and or by the control unit of the stepper motor to communicate the start of the MRE examination. The stepper motor and/or the control unit of the stepper motor may be configured to start the rotation of the gravitation-al transducer once the first TTL is received and accelerates it to the required MRE examination frequency, in particular within a fixed number of dummy shots, for example, within 4 dummy shots. There may be a global TTL counter, e.g., at the control unit, that includes the dummy shots and the further shots termed imaging shots of the MRE acquisition. Additionally, there may be an active TTL counter, that includes only the imaging shots of the MRE. Advantageously via the TTL sent by the MRI system throughout the acquisition, the mechanical vibration of the gravitational transducer may be synchronized with the MRE acquisition particularly efficiently and reliably. Moreover, the exact timing of the MRI system is transferred to the gravitational transducer.

According to a further aspect of the invention, a method for executing a magnetic resonance elastography scan of a subject using a gravitational transducer with a rotating eccentric mass for generating vibrations at a set vibrational frequency is provided. Therein, the rotation of the eccentric mass is driven by a shaft, wherein the rotation of the eccentric mass is synchronized with the corresponding magnetic resonance elastography scan by the method described herein. All features and advantages of the method for synchronizing a rotational eccentric mass of a gravitational transducer with a corresponding magnetic resonance elastography scan may be adapted to the method for executing a magnetic resonance elastography scan and vice versa.

According to a further aspect of the invention, a stepper motor configured to drive a rotational eccentric mass of a gravitational transducer used for a magnetic resonance elastography acquisition carried out by a magnetic resonance imaging system is provided. The rotation of the eccentric mass is driven by a shaft and the stepper motor comprises:
an interface for receiving signals at regular intervals, the signals indicating a start time of an acquisition period of the magnetic resonance elastography acquisition, and for receiving a set vibration frequency of the eccentric mass, wherein the vibration frequency is set such that one or an integer number of rotational periods of the eccentric mass equals an acquisition period, wherein the integer number is the burst count, and the interface is configured to receive the burst count;
a control unit configured to control the stepper motor and comprising programming instructions to carry out the following steps in order to synchronize the eccentric rotational mass with the received signals:
(a) starting the rotation of the eccentric mass at the set vibration frequency; (b) when receiving a signal indicating the start time of an acquisition period, determining the rotational position of the shaft; (c) defining the determined rotational position as first reference position, which the shaft is theoretically expected to occupy at the start time of at least some of the subsequent acquisition periods; (d) depending on the burst count, calculating further reference positions that the shaft is theoretically expected to occupy at the start time of each subsequent acquisition period, wherein the further reference positions may be the same as the first reference position, or may alternate between several positions; (e) at the start time of each subsequent acquisition period of the magnetic resonance scan, determine the current rotational position of the shaft; (f) after each determination of the current rotational position, compare the determined current rotational position with the theoretically expected reference position and decrease or increase the rotational speed of the rotational eccentric mass based on the comparison.

All features and advantages of the method for synchronizing a rotational eccentric mass of a gravitational transducer with a corresponding magnetic resonance elastography scan and of the method for executing a magnetic resonance elastography scan may be adapted to the stepper motor and vice versa. The stepper motor may comprise the motor controller center as descried above. The interface and/or the control unit may be part of the motor controller center. The stepper motor control functions may be implemented in the Phytron MiniLog format, in particular as described in Runge J. H., Hoelzl S. H., Sudakov J. et al., "A novel magnetic resonance elastography transducer concept based on a rotational eccentric mass: preliminary experiences with the gravitational transducer", Phys. Med. Biol. 64:045007 (2019).

According to a further aspect of the invention, a magnetic resonance imaging (MRI) system is provided, The MRI system comprises
a stepper motor as described herein;
a gravitational transducer with an eccentric rotational mass, wherein the rotation of the eccentric mass is driven by a shaft, and the shaft is driven by the stepper motor;
a magnetic resonance scanner including a console for controlling the magnetic resonance scanner, wherein the console is configured to send a signal at regular interval to the stepper motor, in particular to the control unit and/or the interface, the signal indicating the start time of an acquisition interval.

All features and advantages of the method for synchronizing a rotational eccentric mass of a gravitational transducer with a corresponding magnetic resonance elastography scan, of the method for executing a magnetic resonance elastography scan, and of the stepper motor may be adapted to the magnetic resonance imaging system and vice versa.

According to an embodiment, the system comprises a flexible rotating axis, wherein the stepper motor and the gravitational transducer are configured such that rotation of the stepper motor is translated to the shaft of the gravitational transducer via the flexible rotating axis. The flexible rotating axis may be the same flexible rotating axis as described above.

According to a further aspect of the invention, a computer program product for synchronizing a rotational eccentric mass of a gravitational transducer used for a magnetic resonance elastography acquisition with a corresponding magnetic resonance elastography scan carried out by a magnetic resonance imaging system is provided. Therein, the rotation of the eccentric mass is driven by a shaft, and the shaft is driven by a stepper motor, wherein the computer program comprises instructions to cause a control unit of a stepper motor magnetic resonance elastography system to carry out the method as described herein. All features and advantages of the method for synchronizing a rotational eccentric mass of a gravitational transducer with a corresponding magnetic resonance elastography scan, of the method for executing a magnetic resonance elastography scan, of the magnetic resonance imaging system, and of the stepper motor may be adapted to the computer program product and vice versa.

According to a further aspect of the invention, a non-transitory computer-readable medium having stored thereon a computer program product for synchronizing a rotational eccentric mass of a gravitational transducer used for a magnetic resonance elastography acquisition with a corresponding magnetic resonance elastography scan carried out by a magnetic resonance imaging system, wherein the rotation of the eccentric mass is driven by a shaft, and the shaft is driven by a stepper motor, wherein the computer program comprises instructions to cause a control unit of a stepper motor magnetic resonance elastography system to carry out the method as described herein. The computer-readable medium may be any digital storage medium, for example a hard disk, a server, a cloud, a computer, an optical or a magnetic digital storage medium, a CD-ROM, an SSD-card, an SD-card, a DVD or a USB or other memory stick. All features and advantages of the method for synchronizing a rotational eccentric mass of a gravitational transducer with a corresponding magnetic resonance elastography scan, of the method for executing a magnetic resonance elastography scan, of the magnetic resonance imaging system, of the computer program product and of the stepper motor may be adapted to the non-transitory computer-readable medium and vice versa.

All embodiments mentioned herein may be combined with each other.

BRIEF DESCRIPTION OF THE DRAWINGS/FIGURES

The accompanying drawings illustrate various example methods and other example embodiments of various aspects of the invention.

DETAILED DESCRIPTION

Figure 1:
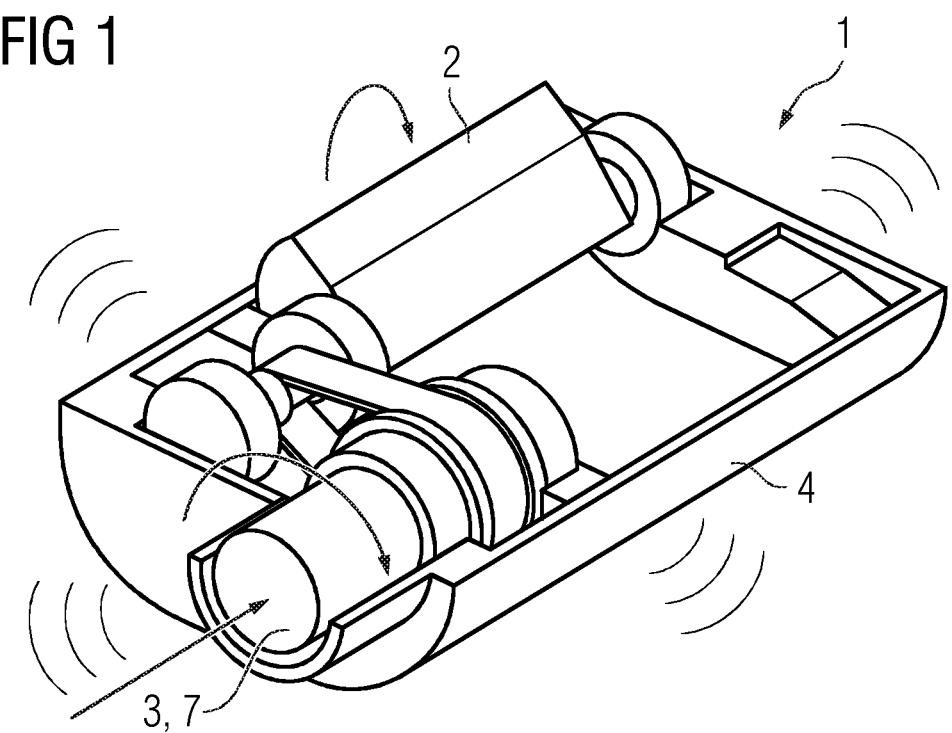
FIG. 1 shows a gravitational transducer according to an embodiment of the invention.

Similar elements are designated with the same reference signs in the drawings.

FIG. 1 shows a gravitational transducer 1 according to an embodiment of the invention. The gravitational transducer 1 comprises a rotational eccentric mass 2 which is driven by a shaft 3 that may be or may be connected to a flexible rotating axis 7. The shaft 3 or the rotating axis 7 may preferably be driven by a stepper motor 6 (not shown here). In this embodiment, the rotation of the shaft 3 is transferred to the eccentric mass 2 via a transmission, in this case a belt transmission, having a certain gear ratio. The gear ratio may for example be 1:3 such that the shaft rotates at f vib/3 while the eccentric mass is rotated at f vib. The rotation of the eccentric mass 2 which is connected to a housing 4 of the gravitational transducer 1 causes the gravitational transducer 1 to vibrate with the rotational frequency f vib of the eccentric mass 2. The gravitational transducer may be fixed to the side of a subject to be examined via MRE in order to introduce the vibrations into the subject during the examination. For example, the gravitational transducer 1 may be used for liver MRE experiments.

Figure 2:
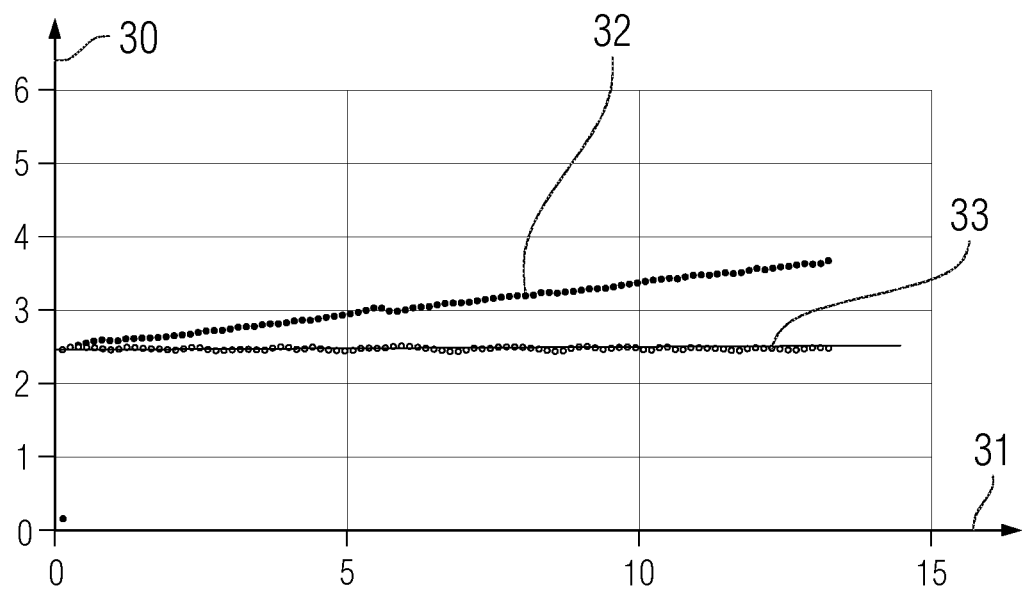
FIG. 2 shows a comparison of the time dependent angular position for a method according to the state of the art and for the method according to the invention.

FIG. 2 shows a comparison of the time dependent angular position 30 in radians at the start times of the consecutive acquisition periods for a method according to the state of the art 32 and for the method according to the invention 33. The horizontal axis 31 shows the examination duration in seconds. As can be seen, the position of the state-of-the-art deviates with the time due to non-ideal synchronization of the MRI system with the stepper motor 6 that drives the eccentric mass 2, while the inventive method leads to a much more stable position at the start times of the acquisition periods. Hence a much more stable MRE signal can be acquired.

Figure 3:
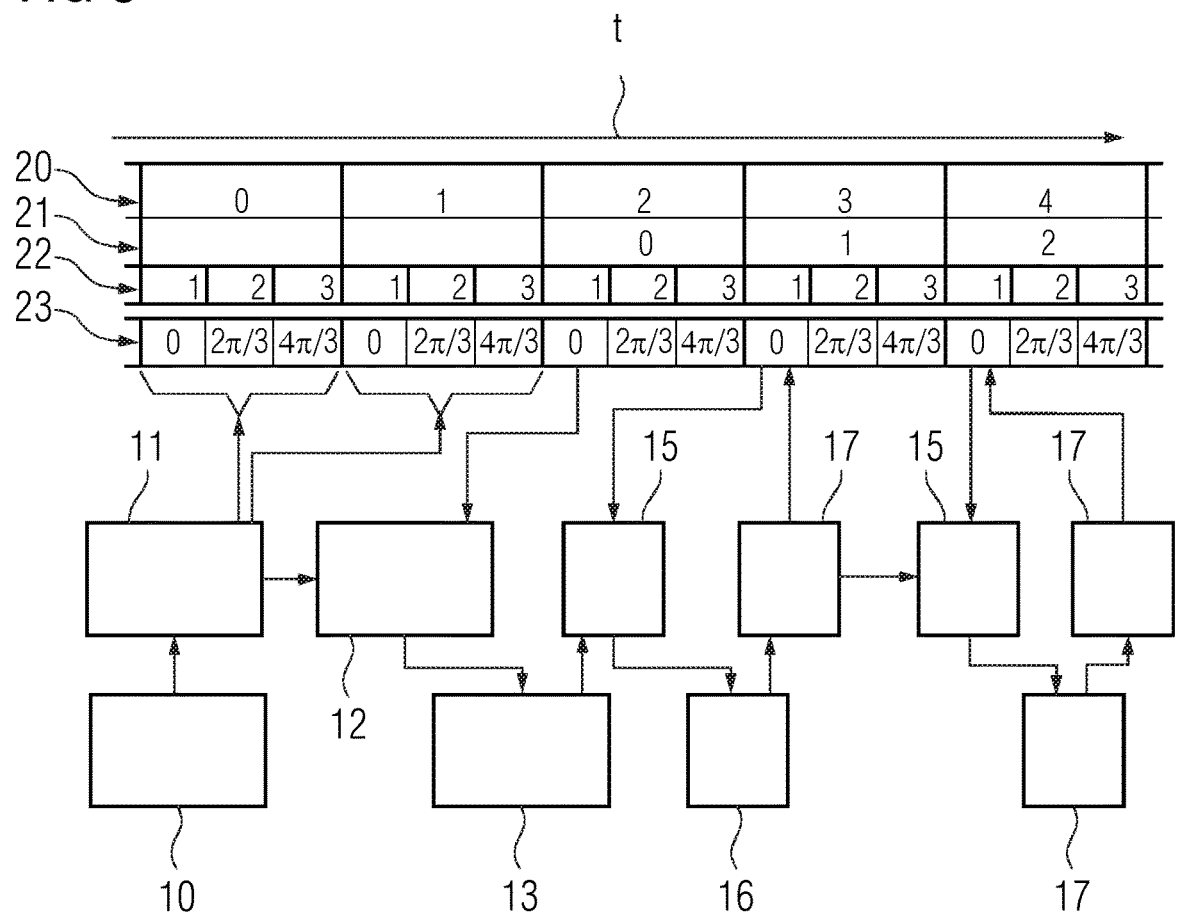
FIG. 3 shows a flow diagram of the method according to an embodiment of the invention.
Figure 5:
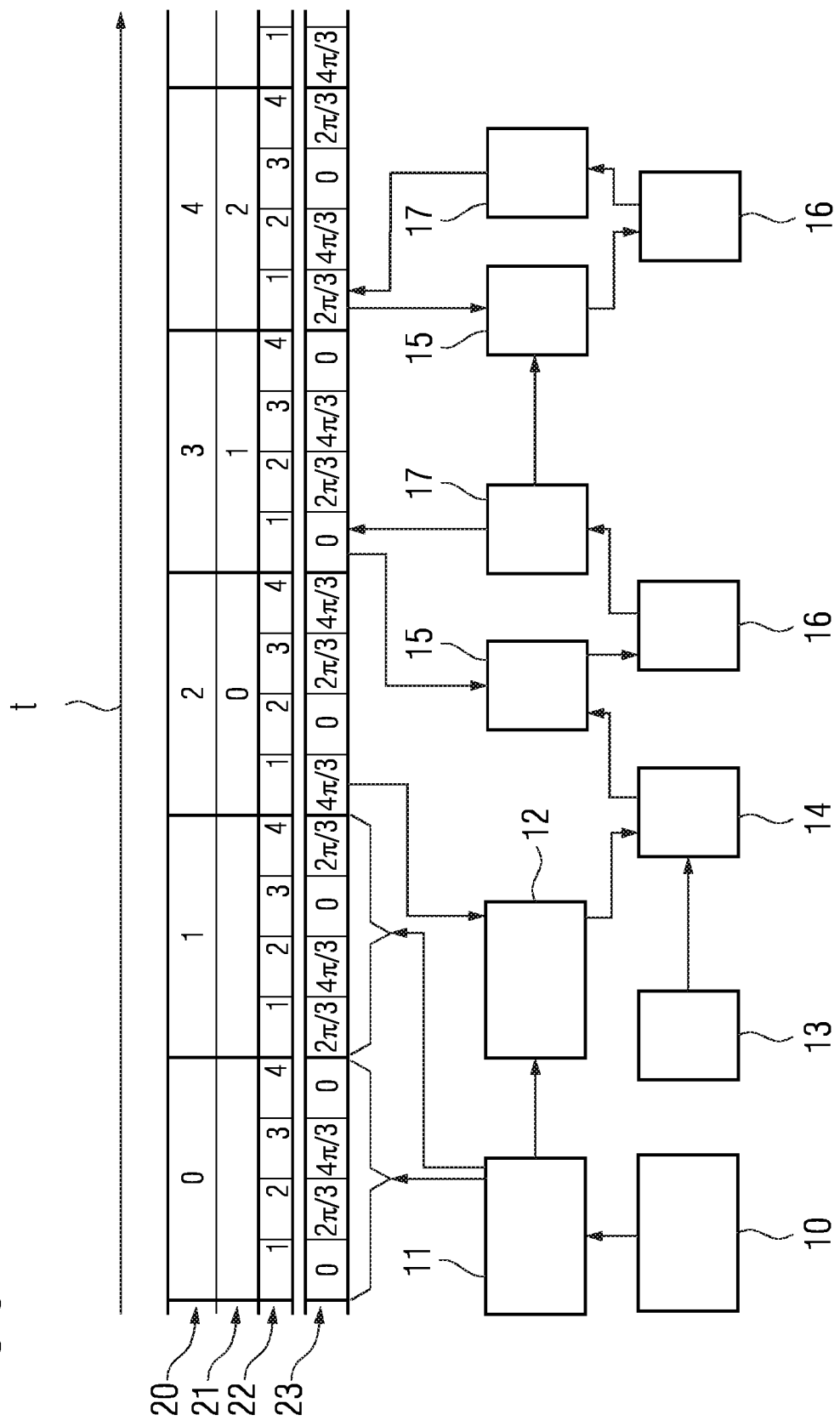
FIG. 5 shows a flow diagram of the method according to an embodiment of the invention.
Figure 7:
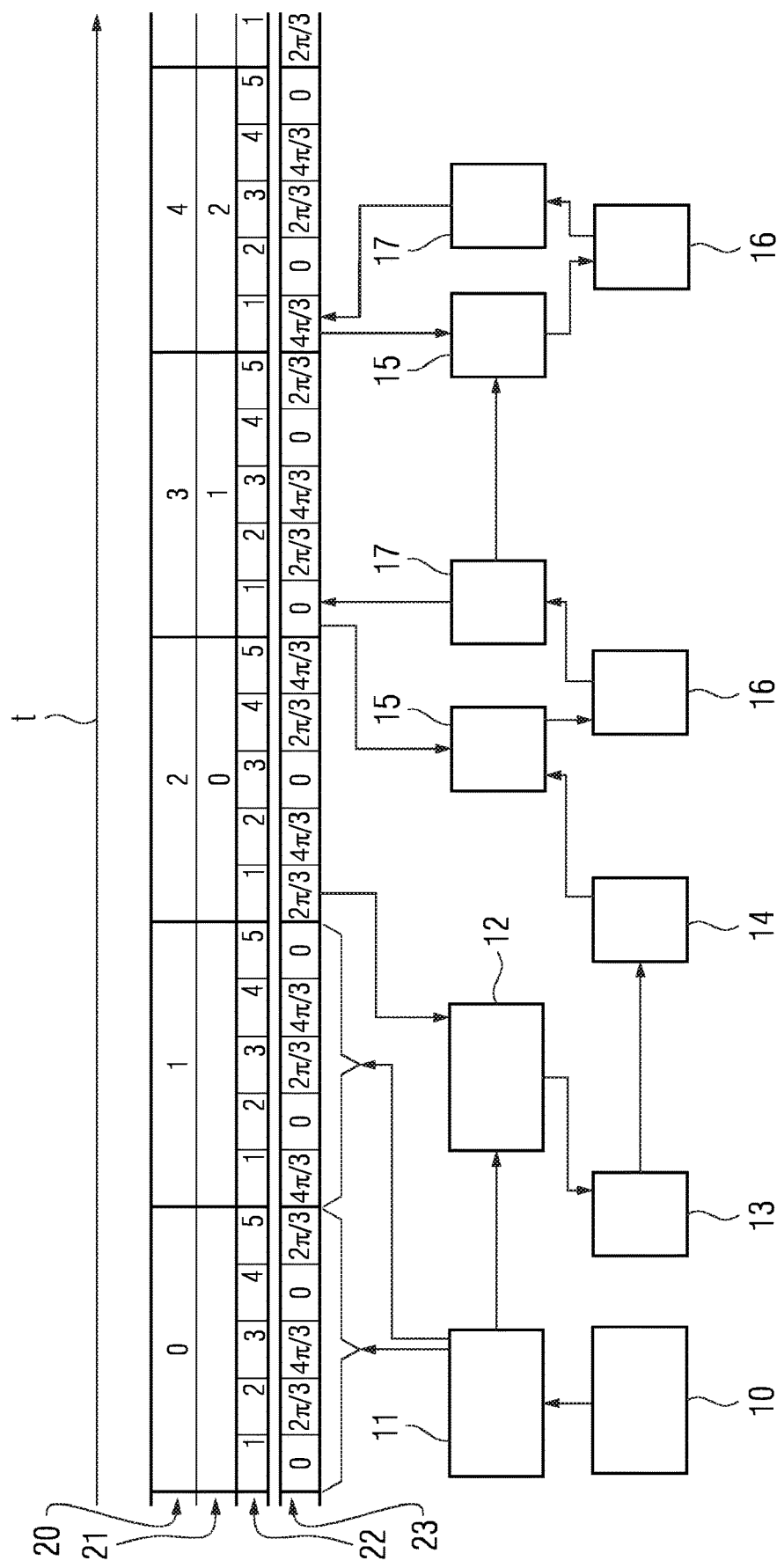
FIG. 7 shows a flow diagram of the method according to an embodiment of the invention.

FIGS. 3, 5 and 7 show a flow diagram of the method according to an embodiment of the invention for synchronizing the eccentric mass 2 with the corresponding MRE scan. On the top table there are columns showing example parameters as the method progresses through time t. In the first line 20, the global TTL number is shown which lists the consecutive TTL signals sent by the MRI system 5 to the stepper motor 6. In the second line 21, the active TTL number is shown, which does not count the TTLs sent during dummy shots 11. The third line 22 shows the burst count which is reset at the beginning of each acquisition period. The fourth line 23 shows the rotational position of the shaft 3. In the examples of FIGS. 3, 5 and 7 the gear ration between the shaft 3 and the eccentric mass 2 is 3:1. Thus, in order that the eccentric mass 2 is be at the same rotational position every burst count, the shaft 3 should be at the same angular position every three burst counts. It should be noted that, in order to get simpler numbers, the phase of the rotation is arbitrarily set to zero in this example, thus the first measured angular/rotational position is 0. The rotational positions 23 as seen here might all be shifted together by any phase shift. Furthermore, it should be noted that the rotational position 23 during the dummy scan is actually not measured and can thus not be known. It is likely that, due to the acceleration of the stepper motor 6 and the eccentric mass 2 at the beginning, the rotational positions 23 during the dummy scans will deviate from the exemplary ones shown here. FIG. 3 shows an example with a burst count of three. Hence, there will only be one reference position, since the expected rotational position 23 of the shaft 3 should be the same at the beginning of each acquisition period.

Figure 4:
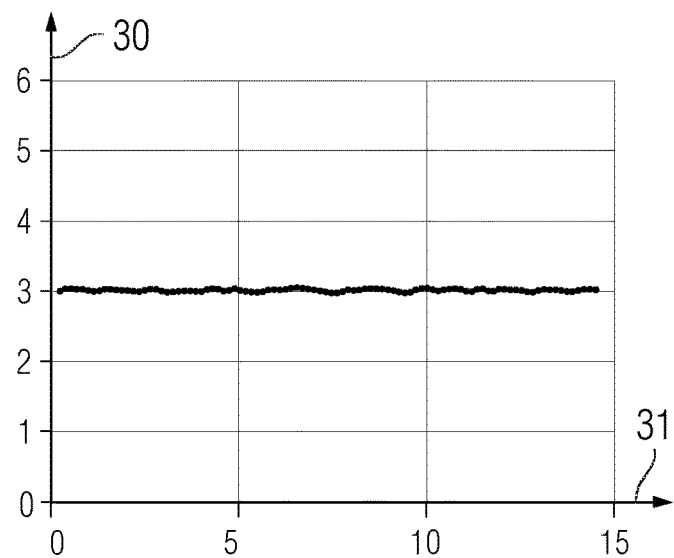
FIG. 4 shows a diagram of the time dependent angular position for one reference position.

According to the method shown in FIG. 3, in a first step 10, the rotation of the eccentric mass 2 is started at a set vibration frequency and the magnetic resonance elastography scan is started at a set acquisition frequency. The vibration frequency is set such that, corresponding to the burst count of three, three rotational periods of the eccentric mass equal an acquisition period. In a next step 11, after starting the rotation of the rotational eccentric mass 2 and the magnetic resonance scan two dummy shots are discarded before the rotational position 23 of the shaft 3 is determined at the start time of the next acquisition period. During this time the active TTL counter remains at zero. In the following step 12, at the start time of the next acquisition period of the magnetic resonance scan, the rotational position 23 of the shaft 3 is determined. The start time of an acquisition period may be triggered by the receipt of a TTL signal from the MRI system. In this example the rotational position is zero. In the next step 13, the determined rotational position is defined as first reference position, which the shaft is theoretically expected to occupy at the start time of the subsequent acquisition periods. Since in this example, there is only one reference position, further reference positions are not calculated here. In the following step 15, at the start time of the next acquisition period of the magnetic resonance scan, the current rotational position of the shaft is determined. In the following step 16, the determined current rotational position is compared with the theoretically expected reference position. Accordingly, in the next step 17, the rotational speed of the rotational eccentric mass 2 is decreased or increased based on the comparison. Steps 15-17 are repeated for the remainder of the examination in order to stabilize the synchronization between the eccentric mass 2 and the MR scan. As can be seen in FIG. 4, this leads to a stable angular position (in radians) 30 at the start time of each acquisition period over time 31. Only minor fluctuations due to the controlling mechanism may occur.

Figure 6:
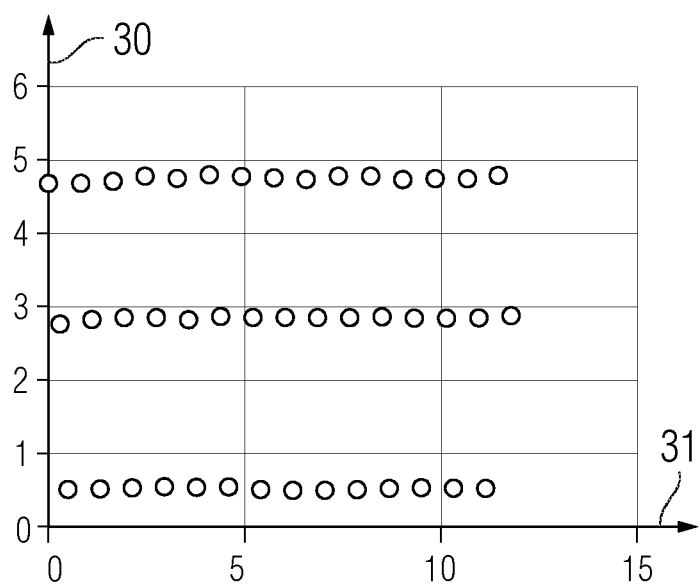
FIG. 6 shows a diagram of the time dependent angular position for three reference positions.

In FIG. 5, where the burst count is 4, and in FIG. 7, where the burst count is 5, two additional reference positions are calculated in step 14 based on the first reference position leading to a total of three reference positions. Hence, in the example of FIG. 5, the set reference positions cycle through the values $4\pi/3$, 0 and $2\pi/3$, while in the example of FIG. 7, the set reference positions cycle through the values $2\pi/3$, 0 and $4\pi/3$. It should be noted again that these angular positions 23 may vary according to an angular offset depending on which reference value is determined in step 12. In both these cases, namely for a burst count of 4 and 5 while having a gear ratio of 3:1, three stable rotational positions are the result as can be seen in FIG. 6, where the angular position 30 in radians at the start times of the acquisition periods is shown vs. the examination duration 31.

Figure 8:
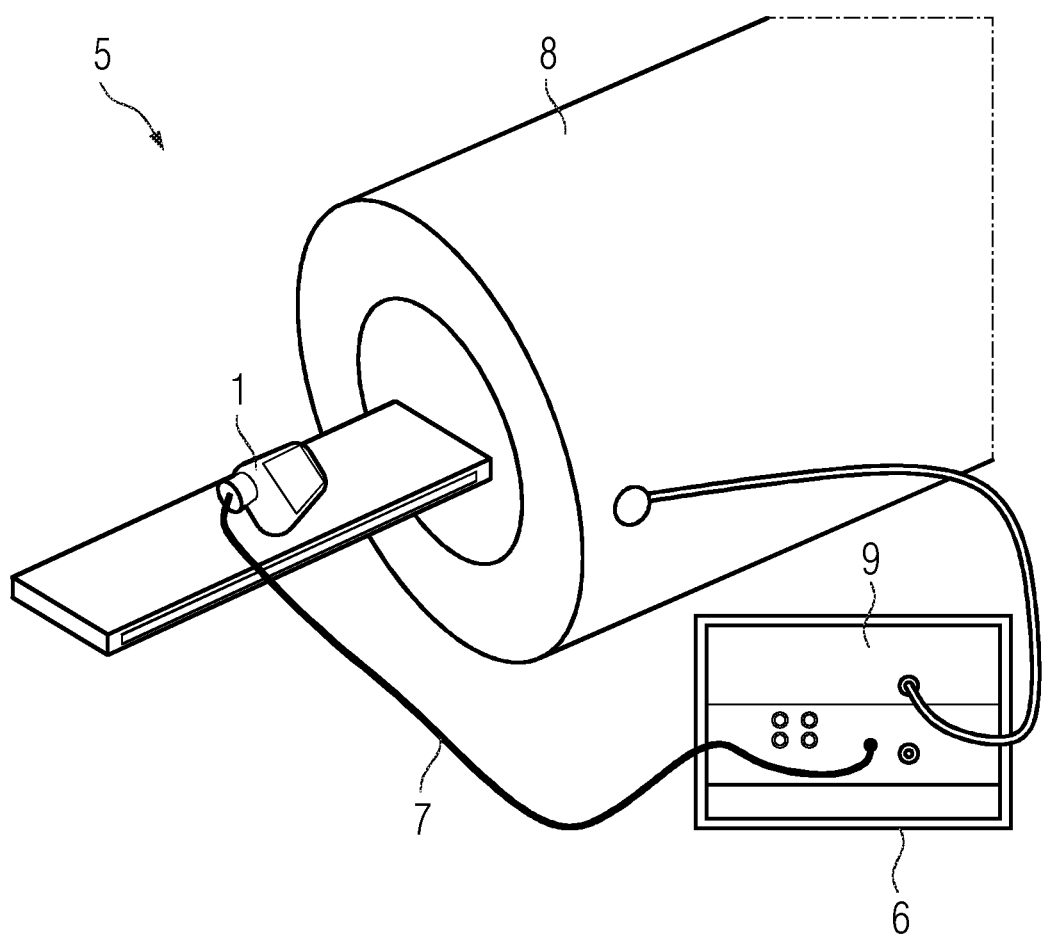
FIG. 8 shows a magnetic resonance imaging system 5 according to an embodiment of the invention.

FIG. 8 shows a magnetic resonance imaging system 5 according to an embodiment of the invention. The system comprises a stepper motor 6 that drives the gravitational transducer 1 as described above via a flexible rotating axis. The stepper motor comprises a control unit that is connected to the MR scanner 8 via an interface 9 in order to allow the inventive synchronization.

What is claimed is:

1. A method for synchronizing a rotational eccentric mass of a gravitational transducer used for a magnetic resonance elastography acquisition with a corresponding magnetic resonance elastography scan carried out by a magnetic resonance imaging system, wherein the rotation of the eccentric mass is driven by a shaft, the method comprising:
   (a) starting the rotation of the eccentric mass at a set vibration frequency and the magnetic resonance elastography scan at a set acquisition frequency, wherein the vibration frequency is set such that one or an integer number of rotational periods of the eccentric mass equals an acquisition period, and wherein the integer number is a burst count;
   (b) at a start time of an acquisition period of the magnetic resonance scan, determining the rotational position of the shaft;
   (c) defining the determined rotational position as first reference position, which the shaft is expected to occupy at the start time of at least some of the subsequent acquisition periods;
   (d) depending on the burst count, calculating further reference positions that the shaft is expected to occupy at the start time of each subsequent acquisition period, wherein the further reference positions are (i) the same as the first reference position, or (ii) alternate between several positions;
   (e) at the start time of each subsequent acquisition period of the magnetic resonance scan, determining a current rotational position of the shaft;
   (f) after each determination of the current rotational position, comparing the determined current rotational position with the expected reference position, and decreasing or increasing the rotational speed of the rotational eccentric mass based on the comparison.

2. The method according to claim 1, wherein after starting the rotation of the rotational eccentric mass and the magnetic resonance scan, a predetermined number of acquisition periods is discarded as dummy shots before the rotational position of the shaft is determined at the start time of a further acquisition period.

3. The method according to claim 1, wherein in step (f) the rotational speed of the shaft is increased:
   (i) if the difference between the respective expected reference position and the determined current position is greater than zero and greater than 7E, or (ii) if the difference between the respective reference position and the current position is less than zero and greater than $-\pi$; and
   wherein in step (f) the rotational speed of the shaft is decreased:
   (i) if the difference between the respective reference position and the current position is greater than zero and less than 7E, or (ii) if the difference between the respective reference position and the current position is less than zero and less than $-\pi$.

4. The method according to claim 1, wherein in step (f) the rotational speed of the shaft is increased or decreased by a fixed amount in each acquisition period.

5. The method according to claim 1, wherein the shaft is driven by a stepper motor, and the rotation of the shaft is transferred to the gravitational transducer via a flexible rotating axis.

6. The method according to claim 5, wherein the rotation of the shaft is translated to rotational eccentric mass of the gravitational transducer with a gear ratio of 1 or higher, such that the rotational eccentric mass rotates faster than the shaft.

7. The method according to claim 6, wherein in step (d), the further reference positions that the shaft is expected to occupy at the start time of each subsequent acquisition period is determined on the basis of the burst-count and the gear ratio.

8. The method according to claim 7, wherein:
   if the gear ratio is three and the burst count is 3, the further reference positions are the same as the first reference positions, and
   if the burst count is 4 or 5, the further reference positions alternate between three different rotational positions.

9. The method according to claim 1, wherein step (e) is triggered by a signal received from the magnetic resonance imaging system at the start time of each acquisition cycle via a transistor-transistor-logic.

10. A method according to claim 1, wherein the magnetic resonance elastography scan is of a subject.

11. A stepper motor configured to drive a rotational eccentric mass of a gravitational transducer used for a magnetic resonance elastography acquisition carried out by a magnetic resonance imaging system, wherein the rotation of the eccentric mass is driven by a shaft, the stepper motor comprising:
   an interface configured to (i) receive signals at regular intervals, the signals indicating a start time of an acquisition period of the magnetic resonance elastography acquisition, (ii) receive a set vibration frequency of the eccentric mass, the vibration frequency being set such that one or an integer number of rotational periods of the eccentric mass equals an acquisition period, the integer number being a burst count, and (iii) receive the burst count;
   a control unit configured to control the stepper motor and comprising programming instructions to carry out the following steps in order to synchronize the eccentric rotational mass with the received signals:
   (a) starting the rotation of the eccentric mass at the set vibration frequency;
   (b) when receiving a signal indicating the start time of an acquisition period, determining the rotational position of the shaft;
   (c) defining the determined rotational position as first reference position, which the shaft is expected to occupy at the start time of at least some of the subsequent acquisition periods;
   (d) depending on the burst count, calculating further reference positions that the shaft is theoretically expected to occupy at the start time of each subsequent acquisition period, wherein the further reference positions are (i) the same as the first reference position, or (ii) alternate between several positions;
   (e) at the start time of each subsequent acquisition period of the magnetic resonance scan, determine a current rotational position of the shaft;
   (f) after each determination of the current rotational position, compare the determined current rotational position with the expected reference position, and decrease or increase the rotational speed of the rotational eccentric mass based on the comparison.

12. A magnetic resonance imaging system, comprising:
   a stepper motor configured to drive a rotational eccentric mass of a gravitational transducer used for a magnetic resonance elastography acquisition carried out by a magnetic resonance imaging system, wherein the rotation of the eccentric mass is driven by a shaft, the stepper motor comprising:
   an interface configured to (i) receive signals at regular intervals, the signals indicating a start time of an acquisition period of the magnetic resonance elastography acquisition, (ii) receive a set vibration frequency of the eccentric mass, the vibration frequency being set such that one or an integer number of rotational periods of the eccentric mass equals an acquisition period, the integer number being a burst count, and (iii) receive the burst count;
   a control unit configured to control the stepper motor and comprising programming instructions to carry out the following steps in order to synchronize the eccentric rotational mass with the received signals:
   (a) starting the rotation of the eccentric mass at the set vibration frequency;
   (b) when receiving a signal indicating the start time of an acquisition period, determining the rotational position of the shaft;
   (c) defining the determined rotational position as first reference position, which the shaft is expected to occupy at the start time of at least some of the subsequent acquisition periods;
   (d) depending on the burst count, calculating further reference positions that the shaft is theoretically expected to occupy at the start time of each subsequent acquisition period, wherein the further reference positions are (i) the same as the first reference position, or (ii) alternate between several positions;
   (e) at the start time of each subsequent acquisition period of the magnetic resonance scan, determine a current rotational position of the shaft;
   (f) after each determination of the current rotational position, compare the determined current rotational position with the expected reference position, and decrease or increase the rotational speed of the rotational eccentric mass based on the comparison;
   a gravitational transducer with an eccentric rotational mass, wherein the rotation of the eccentric mass is driven by a shaft, and the shaft is driven by the stepper motor; and
   a magnetic resonance scanner including a console for controlling the magnetic resonance scanner,
   wherein the console is configured to transmit a signal at regular intervals to the stepper motor, the signal indicating the start time of an acquisition interval.

13. The system according to claim 12,
   wherein the system comprises a flexible rotating axis, and
   wherein the stepper motor and the gravitational transducer are each configured such that rotation of the stepper motor is translated to the shaft of the gravitational transducer via the flexible rotating axis.

14. A non-transitory computer-readable medium having stored thereon a computer program product for synchronizing a rotational eccentric mass of a gravitational transducer used for a magnetic resonance elastography acquisition with a corresponding magnetic resonance elastography scan carried out by a magnetic resonance imaging system, wherein the rotation of the eccentric mass is driven by a shaft, and the shaft is driven by a stepper motor,
   wherein the computer program comprises instructions to cause a control unit of a stepper motor magnetic resonance elastography system to:
   (a) start the rotation of the eccentric mass at a set vibration frequency and the magnetic resonance elastography scan at a set acquisition frequency, wherein the vibration frequency is set such that one or an integer number of rotational periods of the eccentric mass equals an acquisition period, wherein the integer number is a burst count;

(b) at a start time of an acquisition period of the magnetic resonance scan, determine the rotational position of the shaft;
(c) define the determined rotational position as first reference position, which the shaft is expected to occupy at the start time of at least some of the subsequent acquisition periods;
(d) depending on the burst count, calculate further reference positions that the shaft is expected to occupy at the start time of each subsequent acquisition period, wherein the further reference positions are (i) the same as the first reference position, or (ii) alternate between several positions;
(e) at the start time of each subsequent acquisition period of the magnetic resonance scan, determine a current rotational position of the shaft;
(f) after each determination of the current rotational position, compare the determined current rotational position with the expected reference position, and decrease or increase the rotational speed of the rotational eccentric mass based on the comparison.

* * * * *